(12) United States Patent
Cassin et al.

(10) Patent No.: US 9,320,689 B2
(45) Date of Patent: Apr. 26, 2016

(54) COSMETIC COMPOSITION COMPRISING SILICA AEROGELS PARTICLES AND HYDROCARBON-BASED OILS

(75) Inventors: Guillaume Cassin, Villebon sur Yvette (FR); Sylvie Poret Fristot, Rungis (FR)

(73) Assignee: L'OREAL, Paris (FR)

( * ) Notice: Subject to any disclaimer, the term of this patent is extended or adjusted under 35 U.S.C. 154(b) by 32 days.

(21) Appl. No.: 13/996,925

(22) PCT Filed: Dec. 19, 2011

(86) PCT No.: PCT/EP2011/073188
§ 371 (c)(1),
(2), (4) Date: Jul. 9, 2013

(87) PCT Pub. No.: WO2012/084781
PCT Pub. Date: Jun. 28, 2012

(65) Prior Publication Data
US 2013/0287828 A1    Oct. 31, 2013

Related U.S. Application Data

(60) Provisional application No. 61/436,272, filed on Jan. 26, 2011.

(30) Foreign Application Priority Data

Dec. 21, 2010  (FR) ..................... 10 60894

(51) Int. Cl.
*A61Q 19/00*   (2006.01)
*A61Q 1/00*    (2006.01)
*A61K 8/04*    (2006.01)
*A61K 8/25*    (2006.01)
*A61K 8/31*    (2006.01)
*A61K 8/37*    (2006.01)

(52) U.S. Cl.
CPC . *A61K 8/042* (2013.01); *A61K 8/25* (2013.01); *A61K 8/31* (2013.01); *A61K 8/37* (2013.01); *A61K 8/375* (2013.01); *A61Q 19/00* (2013.01); *A61Q 19/008* (2013.01)

(58) Field of Classification Search
None
See application file for complete search history.

(56) References Cited

U.S. PATENT DOCUMENTS

| 5,800,816 A * | 9/1998 | Brieva et al. ................. 424/63 |
| 5,911,974 A | 6/1999 | Brieva et al. |
| 5,965,112 A | 10/1999 | Brieva et al. |
| 5,985,298 A | 11/1999 | Brieva et al. |
| 6,464,964 B1 | 10/2002 | Brieva et al. |
| 2003/0007987 A1 | 1/2003 | Brieva et al. |
| 2003/0147931 A1 | 8/2003 | Brieva et al. |
| 2004/0175345 A1 | 9/2004 | Brieva et al. |
| 2006/0088562 A1 | 4/2006 | Brieva et al. |
| 2007/0092468 A1 | 4/2007 | Brieva et al. |
| 2009/0247648 A1 * | 10/2009 | Zhao ............................ 514/772 |
| 2012/0065163 A1 | 3/2012 | Zhao |

FOREIGN PATENT DOCUMENTS

WO    WO 2009/120602 A1    10/2009

OTHER PUBLICATIONS

International Search Report issued Dec. 3, 2012, in PCT/EP2011/073188.
"Dow Corning® VM-2270 Aerogel Fine Particles", Dow Corning, http://www2.dowcorning.com/DataFiles/090007c88020e235.pdf XP 002650585, Apr. 2009, 5 pages.
"Silica Silylate Aerogel for Cosmetic Applications", IP.COM Journal, XP 013112635, Jan. 30, 2006, 3 pages.

* cited by examiner

*Primary Examiner* — H. Sarah Park
(74) *Attorney, Agent, or Firm* — Oblon, McClelland, Maier & Neustadt, L.L.P.

(57) ABSTRACT

The present invention relates to a composition comprising a mixture of: hydrophobic silica aerogel particles with a specific surface area per unit of mass ($S_M$) ranging from 500 to 1500 m²/g and a size expressed as the mean volume diameter (D[0.5]) ranging from 1 to 1500 μm, and at least a first and at least a second hydrocarbon-based oil chosen from branched esters, pentaerythritol esters, hydrogenated polyolefins and fatty acid triglycerides, and mixtures thereof, the first hydrocarbon-based oil being present in a content of greater than or equal to 40% by weight of the mixture of the first and second oils.

10 Claims, No Drawings

COSMETIC COMPOSITION COMPRISING SILICA AEROGELS PARTICLES AND HYDROCARBON-BASED OILS

The invention relates to a cosmetic composition for keratin materials, especially the skin, the lips, the hair and the nails. The invention also relates to a cosmetic process for treating keratin materials using the said composition.

In the field of skincare cosmetic compositions, it is known practice to use mineral or organic fillers with a "soft focus" effect which absorb sebum and perspiration, for making the skin matt and/or optically smoothing the microrelief and concealing skin imperfections.

However, the use of these fillers is generally accompanied by a dry, coarse feel and a lack of comfort, which users find unacceptable.

Silicone elastomers are also widely used as matting agents since they afford a soft feel on the skin, but must be used in relatively large amount in order to have a matting effect, which constitutes an impediment in the choice of the texture and in the cost of the formulation.

There is thus still a need for matting cosmetic compositions and/or cosmetic compositions for masking skin imperfections, which have good cosmetic properties, an in particular which are gentle on application and less restrictive in terms of cost.

The Applicant has discovered that this need can be satisfied by combining in a composition hydrophobic silica aerogels particles and a mixture of specific hydrocarbon-based oils.

More specifically, the present invention relates to a cosmetic composition comprising a mixture of:
hydrophobic silica aerogel particles with a specific surface area per unit of mass ($S_M$) ranging from 500 to 1500 $m^2/g$ and a size expressed as the mean volume diameter (D[0.5]) ranging from 1 to 1500 µm,
at least a first hydrocarbon-based oil and
at least a second hydrocarbon-based oil chosen from pentaerythritol esters, hydrogenated polyolefins and fatty acid triglycerides, and mixtures thereof, the first hydrocarbon-based oil being present in a content of greater than or equal to 40% by weight of the mixture of first and second oils.

The first hydrocarbon-based oil and the second hydrocarbon-based oil are different from each other.

The mixture of silica aerogel particles and hydrocarbon-based oils makes it possible to obtain compositions that are comfortable and gentle on application, which have matting and soft focus properties. It may be used partially or totally to replace the silicone elastomers used for obtaining these properties.

The mixture of hydrophobic silica aerogel particles and hydrocarbon-based oils is advantageously in the form of a gel that does not flow under its own weight.

A subject of the present invention is also a mixture of:
hydrophobic silica aerogel particles with a specific surface area per unit of mass ($S_M$) ranging from 500 to 1500 $m^2/g$ and a size expressed as the mean volume diameter (D[0.5]) ranging from 1 to 1500 µm, and
at least a first hydrocarbon-based oil and
at least a second hydrocarbon-based oil chosen from pentaerythritol esters, hydrogenated polyolefins and fatty acid triglycerides, and mixtures thereof, the first hydrocarbon-based oil being present in a content of greater than or equal to 40% by weight of the mixture of first and second oils.

A subject of the present invention is also a cosmetic process for making up and/or caring for keratin materials, comprising a step of applying a composition as defined above to the said materials.

Hydrophobic Silica Aerogels:

Silica aerogels are porous materials obtained by replacing (by drying) the liquid component of a silica gel with air.

They are generally synthesized via a sol-gel process in liquid medium and then dried, usually by extraction of a supercritical fluid, the one most commonly used being supercritical $CO_2$. This type of drying makes it possible to avoid shrinkage of the pores and of the material. The sol-gel process and the various drying processes are described in detail in Brinker C J., and Scherer G. W., Sol-Gel Science: New York: Academic Press, 1990.

The hydrophobic silica aerogel particles used in the present invention have a specific surface area per unit of mass ($S_M$) ranging from 500 to 1500 $m^2/g$, preferably from 600 to 1200 $m^2/g$ and better still from 600 to 800 $m^2/g$, and a size expressed as the mean volume diameter (D[0.5]), ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles used in the present invention have a size expressed as the mean volume diameter (D[0.5]) ranging from 1 to 30 µm, preferably from 5 to 25 µm, better still from 5 to 20 µm and even better still from 5 to 15 µm.

The specific surface area per unit of mass may be determined via the BET (Brunauer-Emmett-Teller) nitrogen absorption method described in the *Journal of the American Chemical Society*, vol. 60, page 309, February 1938 and corresponding to the international standard ISO 5794/1 (appendix D). The BET specific surface area corresponds to the total specific surface area of the particles under consideration.

The size of the silica aerogel particles may be measured by static light scattering using a commercial granulometer such as the MasterSizer 2000 machine from Malvern. The data are processed on the basis of the Mie scattering theory. This theory, which is exact for isotropic particles, makes it possible to determine, in the case of non-spherical particles, an "effective" particle diameter. This theory is especially described in the publication by Van de Hulst, H. C., "Light Scattering by Small Particles," Chapters 9 and 10, Wiley, New York, 1957.

According to one advantageous embodiment, the hydrophobic silica aerogel particles used in the present invention have a specific surface area per unit of mass ($S_M$) ranging from 600 to 800 $m^2/g$ and a size expressed as the mean volume diameter (D[0.5]) ranging from 5 to 20 µm and better still from 5 to 15 µm.

The silica aerogel particles used in the present invention may advantageously have a tamped density (ρ) ranging from 0.04 $g/cm^3$ to 0.10 $g/cm^3$ and preferably from 0.05 $g/cm^3$ to 0.08 $g/cm^3$.

In the context of the present invention, this density, known as the tamped density, may be assessed according to the following protocol:

40 g of powder are poured into a measuring cylinder; the measuring cylinder is then placed on a Stav 2003 machine from Stampf Volumeter; the measuring cylinder is then subjected to a series of 2500 packing motions (this operation is repeated until the difference in volume between two consecutive tests is less than 2%); the final volume Vf of packed powder is then measured directly on the measuring cylinder. The tamped density is determined by the ratio m/Vf, in this instance 40/Vf (Vf being expressed in $cm^3$ and m in g).

According to one embodiment, the hydrophobic silica aerogel particles used in the present invention have a specific surface area per unit of volume $S_V$ ranging from 5 to 60 m$^2$/cm$^3$, preferably from 10 to 50 m$^2$/cm$^3$ and better still from 15 to 40 m$^2$/cm$^3$. The specific surface area per unit of volume is given by the relationship: $S_V=S_M \times \rho$, where $\rho$ is the tamped density expressed in g/cm$^3$ and $S_M$ is the specific surface area per unit of mass expressed in m$^2$/g, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The oil-absorbing capacity measured at the wet point, noted Wp, corresponds to the amount of water that needs to be added to 100 g of particle in order to obtain a homogeneous paste. It is measured according to the wet point method or the method for determining the oil uptake of a powder described in standard NF T 30-022. It corresponds to the amount of oil adsorbed onto the available surface of the powder and/or absorbed by the powder by measuring the wet point, described below:

An amount m=2 g of powder is placed on a glass plate, and the oil (isononyl isononanoate) is then added dropwise. After addition of 4 to 5 drops of oil to the powder, mixing is performed using a spatula, and addition of oil is continued until a conglomerate of oil and powder has formed. At this point, the oil is added one drop at a time and the mixture is then triturated with the spatula. The addition of oil is stopped when a firm, smooth paste is obtained. This paste must be able to be spread on the glass plate without cracking or forming lumps. The volume Vs (expressed in ml) of oil used is then noted.

The oil uptake corresponds to the ratio Vs/m.

The aerogels used according to the present invention are hydrophobic silica aerogels, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalized the OH groups with silyl groups Si—Rn, for example trimethylsilyl groups.

As regards the preparation of hydrophobic silica aerogels particles that have been surface-modified by silylation, reference may be made to document U.S. Pat. No. 7,470,725.

Use will be made in particular of hydrophobic silica aerogels particles surface-modified with trimethylsilyl groups (trimethylsilyl silica).

As hydrophobic silica aerogels that may be used in the invention, examples that may be mentioned include the aerogel sold under the name VM-2260 (INCI name: Silica silylate), by the company Dow Corning, the particles of which have a mean size of about 1000 microns and a specific surface area per unit of mass ranging from 600 to 800 m$^2$/g.

Mention may also be made of the aerogels sold by the company Cabot under the references AEROGEL TLD 201, AEROGEL OGD 201, AEROGEL TLD 203, ENOVA® AEROGEL MT 1100, ENOVA AEROGEL MT 1200.

Use will be made more particularly of the aerogel sold under the name VM-2270 (INCI name: Silica silylate), by the company Dow Corning, the particles of which have a mean size ranging from 5-15 microns and a specific surface area per unit of mass ranging from 600 to 800 m$^2$/g.

The silica aerogel particles may represent from 0.5% to 30% by weight, preferably from 1% to 20% by weight, better still from 2% to 15% by weight, more preferably from 5% to 10% by weight and even better still from 7% to 9% by weight of the mixture (hydrocarbon-based oils and silica aerogels) according to the invention.

The silica aerogel particles may be present in the composition according to the invention in a content ranging from 0.05% to 15% by weight, preferably from 0.1% to 10% by weight, better still from 0.5% to 5% by weight and more preferably from 0.5% to 2% by weight relative to the total weight of the composition.

First and Second Hydrocarbon-Based Oils:

The composition according to the invention comprises at least a first hydrocarbon-based oil and at least a second hydrocarbon-based oil chosen from pentaerythritol esters, hydrogenated polyolefins and fatty acid triglycerides, and mixtures thereof, the first hydrocarbon-based oil being present in a content of greater than or equal to 40%, preferably greater than or equal to 50% by weight and better still greater than or equal to 55% by weight relative to the weight of the mixture of first and second hydrocarbon-based oils.

The term "oil" means a fatty substance that is liquid at room temperature (25° C.) and at atmospheric pressure.

The first hydrocarbon-based oil may be present in a content ranging from 40% to 80%, preferably from 50% to 70% by weight and better still from 55% to 65% by weight relative to the weight of the mixture of first and second hydrocarbon-based oils.

The second hydrocarbon-based oil may be present in a content of less than 60% by weight, better still less than or equal to 50% by weight relative to the weight of the mixture of first and second hydrocarbon-based oils, for example ranging from 20% to 59% by weight, preferably from 30% to 50% by weight and better still from 35% to 45% by weight relative to the weight of the mixture of first and second hydrocarbon-based oils.

The mixture of first and second hydrocarbon-based oils may represent from 80% to 99% by weight, preferably from 85% to 98% by weight and better still from 90% to 95% by weight relative to the total weight of the mixture (hydrocarbon-based oils and silica aerogels).

First Hydrocarbon-Based Oil

The first hydrocarbon-based oil may be chosen from any hydrocarbon-based oil. It may be chosen, for example, from branched alkanes, linear alkanes, esters, which are preferably branched, pentaerythritol esters, hydrogenated polyolefins and fatty acid triglycerides, and mixtures thereof.

The first hydrocarbon-based oil may be chosen advantageously from branched alkanes, linear alkanes, and esters, which are preferably branched.

The branched alkanes used in the present invention preferably comprise from 8 to 16 carbon atoms and may be chosen from isododecane, isodecane and isohexadecane, and mixtures thereof; isohexadecane is preferably used.

The linear alkanes are preferably volatile.

A "volatile linear alkane" that is suitable for the invention means a cosmetic linear alkane, which is capable of evaporating on contact with the skin in less than one hour, at room temperature (25° C.) and atmospheric pressure (760 mmHg, i.e. 101 325 Pa), which is liquid at room temperature, especially having an evaporation rate ranging from 0.01 to 15 mg/cm$^2$/min, at room temperature (25° C.) and atmospheric pressure (760 mmHg).

Preferably, the "volatile linear alkanes" that are suitable for use in the invention have an evaporation rate ranging from 0.01 to 3.5 mg/cm$^2$/minute, at room temperature (25° C.) and atmospheric pressure (760 mmHg).

Preferably, the "volatile linear alkanes" that are suitable for use in the invention have an evaporation rate ranging from 0.01 to 1.5 mg/cm$^2$/minute, at room temperature (25° C.) and atmospheric pressure (760 mmHg).

More preferably, the "volatile linear alkanes" that are suitable for use in the invention have an evaporation rate ranging from 0.01 to 0.8 mg/cm$^2$/minute, at room temperature (25° C.) and atmospheric pressure (760 mmHg).

Even more preferably, the "volatile linear alkanes" that are suitable for use in the invention have an evaporation rate ranging from 0.01 to 0.3 mg/cm$^2$/minute, at room temperature (25° C.) and atmospheric pressure (760 mmHg).

Even more preferably, the "volatile linear alkanes" that are suitable for use in the invention have an evaporation rate ranging from 0.01 to 0.12 mg/cm$^2$/minute, at room temperature (25° C.) and atmospheric pressure (760 mmHg).

The evaporation rate of a volatile alkane in accordance with the invention (and more generally of a volatile solvent) may especially be evaluated by means of the protocol described in WO 06/013 413, and more particularly by means of the protocol described below.

15 g of volatile hydrocarbon-based solvent are placed in a crystallizing dish (diameter: 7 cm) placed on a balance that is in a chamber of about 0.3 m$^3$ with regulated temperature (25° C.) and hygrometry (50% relative humidity).

The liquid is allowed to evaporate freely, without stirring, while providing ventilation by means of a ventilator (Papst-Motoren, reference 8550 N, rotating at 2700 rpm) placed vertically above the crystallizing dish containing the volatile hydrocarbon-based solvent, the blades being directed toward the crystallizing dish, 20 cm away from the bottom of the crystallizing dish.

The mass of volatile hydrocarbon-based solvent remaining in the crystallizing dish is measured at regular time intervals.

The evaporation profile of the solvent is then obtained by plotting the curve of the amount of product evaporated (in mg/cm$^2$) as a function of time (in minutes).

The evaporation rate is then calculated, which corresponds to the tangent to the origin of the curve obtained. The evaporation rates are expressed in mg of volatile solvent evaporated per unit area (cm$^2$) and per unit of time (minutes).

According to one preferred embodiment, the "volatile linear alkanes" that are suitable for use in the invention have a non-zero vapour pressure (also known as the saturating vapour pressure), at room temperature, in particular a vapour pressure ranging from 0.3 Pa to 6000 Pa.

Preferably, the "volatile linear alkanes" that are suitable for use in the invention have a vapour pressure ranging from 0.3 to 2000 Pa, at room temperature (25° C.).

Preferably, the "volatile linear alkanes" that are suitable for use in the invention have a vapour pressure ranging from 0.3 to 1000 Pa, at room temperature (25° C.).

More preferably, the "volatile linear alkanes" that are suitable for use in the invention have a vapour pressure ranging from 0.4 to 600 Pa, at room temperature (25° C.).

Preferably, the "volatile linear alkanes" that are suitable for use in the invention have a vapour pressure ranging from 1 to 200 Pa, at room temperature (25° C.).

More preferably, the "volatile linear alkanes" that are suitable for use in the invention have a vapour pressure ranging from 3 to 60 Pa, at room temperature (25° C.).

According to one embodiment, a volatile linear alkane that is suitable for use in the invention may have a flash point that is in the range from 30 to 120° C. and more particularly from 40 to 100° C. The flash point is in particular measured according to standard ISO 3679.

According to one embodiment, an alkane that is suitable for use in the invention may be a volatile linear alkane comprising from 7 to 14 carbon atoms.

Preferably, the "volatile linear alkanes" that are suitable for use in the invention comprise from 8 to 14 carbon atoms.

Preferably, the "volatile linear alkanes" that are suitable for use in the invention comprise from 9 to 14 carbon atoms.

Preferably, the "volatile linear alkanes" that are suitable for use in the invention comprise from 10 to 14 carbon atoms.

Preferably, the "volatile linear alkanes" that are suitable for use in the invention comprise from 11 to 14 carbon atoms.

According to one advantageous embodiment, the "volatile linear alkanes" that are suitable for use in the invention have an evaporation rate, as defined above, ranging from 0.01 to 3.5 mg/cm$^2$/minute, at room temperature (25° C.) and atmospheric pressure (760 mmHg), and comprise from 8 to 14 carbon atoms.

A volatile linear alkane that is suitable for use in the invention may advantageously be of plant origin.

Preferably, the volatile linear alkane or the mixture of volatile linear alkanes present in the composition according to the invention comprises at least one $^{14}$C (carbon-14) carbon isotope. In particular, the $^{14}$C isotope may be present in a $^{14}$C/$^{12}$C ratio of greater than or equal to $1\times10^{-16}$, preferably greater than or equal to $1\times10^{-15}$, more preferably greater than or equal to $7.5\times10^{-14}$ and better still greater than or equal to $1.5\times10^{-13}$. Preferably, the ratio $^{14}$C/$^{12}$C ranges from $6\times10^{-13}$ to $1.2\times10^{-12}$.

The amount of $^{14}$C isotopes in the volatile linear alkane or the mixture of volatile linear alkanes may be determined via methods known to those skilled in the art such as the Libby compacting method, liquid scintillation spectrometry or accelerator mass spectrometry.

Such an alkane may be obtained, directly or in several steps, from a plant raw material, such as an oil, a butter, a wax, etc.

As examples of alkanes that are suitable for use in the invention, mention may be made of the alkanes described in patents WO 2007/068 371 or WO 2008/155 059 of the company Cognis (mixtures of different alkanes differing by at least one carbon). These alkanes are obtained from fatty alcohols, which are themselves obtained from coconut oil or palm oil.

As examples of linear alkanes that are suitable for use in the invention, mention may be made of n-heptane (C7), n-octane (C8), n-nonane (C9), n-decane (C10), n-undecane (C11), n-dodecane (C12), n-tridecane (C13) and n-tetradecane (C14), and mixtures thereof. According to one particular embodiment, the volatile linear alkane is chosen from n-nonane, n-undecane, n-dodecane, n-tridecane and n-tetradecane, and mixtures thereof.

According to one preferred mode, mention may be made of mixtures of n-undecane (C11) and of n-tridecane (C13) obtained in Examples 1 and 2 of patent application WO 2008/155 059 from the company Cognis.

Mention may also be made of n-dodecane (C12) and n-tetradecane (C14) such as those sold by Sasol under the references, respectively, Parafol 12-97 and Parafol 14-97, and also mixtures thereof.

The volatile linear alkane may also be used alone.

Alternatively or preferentially, a mixture of two different volatile liquid linear alkanes, differing from each other by a carbon number n of at least 1, in particular differing from each other by a carbon number of 1 or 2, may be used.

According to a first embodiment, a mixture of at least two different volatile linear alkanes comprising from 10 to 14 carbon atoms and differing from each other by a carbon number of at least 1 may be used. Examples that may especially be mentioned include mixtures of C10/C11, C11/C12 or C12/C13 volatile linear alkanes.

According to another embodiment, a mixture of at least two different linear alkanes, which are preferably volatile, comprising from 10 to 14 carbon atoms and differing from each other by a carbon number of at least 2 may be used. Examples that may especially be mentioned include mixtures of C10/C12 or C12/C14 volatile linear alkanes, for an even carbon number n and the C11/C13 mixture for an odd carbon number n.

According to one preferred mode, a mixture of at least two different linear alkanes, which are preferably volatile, comprising from 10 to 14 carbon atoms and differing from each other by a carbon number of at least 2, and in particular a mixture of C11/C13 volatile linear alkanes or a mixture of C12/C14 volatile linear alkanes, is used.

Other mixtures combining more than two volatile linear alkanes according to the invention, for instance a mixture of at least three different linear alkanes, which are preferably volatile, comprising from 7 to 14 carbon atoms and differing from each other by a carbon number of at least 1, also form part of the invention, but mixtures of two volatile linear alkanes according to the invention are preferred (binary mixtures), the said two volatile linear alkanes preferably representing more than 95% and better still more than 99% by weight of the total content of volatile linear alkanes in the mixture.

According to one particular mode of the invention, in a mixture of linear alkanes, which are preferably volatile, the linear alkane having the smaller carbon number is predominant in the mixture.

According to another mode of the invention, a mixture of linear alkanes, which are preferably volatile, in which the linear alkane having the larger carbon number is predominant in the mixture is used.

As examples of mixtures that are suitable for use in the invention, mention may be made especially of the following mixtures:
  from 50% to 90% by weight, preferably from 55% to 80% by weight and more preferentially from 60% to 75% by weight of Cn liquid volatile linear alkane with n ranging from 7 to 14,
  from 10% to 50% by weight, preferably from 20% to 45% by weight and preferably from 24% to 40% by weight of Cn+x liquid volatile linear alkane with x greater than or equal to 1, preferably x=1 or x=2, with n+x between 8 and 14,
relative to the total weight of alkanes in the said mixture.

In particular, the said mixture of alkanes according to the invention contains:
  less than 2% by weight and preferably less than 1% by weight of branched hydrocarbons,
  and/or less than 2% by weight and preferably less than 1% by weight of aromatic hydrocarbons,
  and/or less than 2% by weight and preferably less than 1% by weight and preferentially less than 0.1% by weight of unsaturated hydrocarbons in the mixture.

More particularly, a volatile linear alkane that is suitable for use in the invention may be used in the form of an n-undecane/n-tridecane mixture.

In particular, use will be made of a mixture of volatile linear alkanes comprising:
  from 55% to 80% by weight and preferably from 60% to 75% by weight of C11 liquid volatile linear alkane (n-undecane),
  from 20% to 45% by weight and preferably from 24% to 40% by weight of C13 volatile linear alkane (n-tridecane),
relative to the total weight of alkanes in the said mixture.

According to one particular embodiment, the mixture of alkanes is an n-undecane/n-tridecane mixture. In particular, such a mixture may be obtained according to Example 1 or Example 2 of WO 2008/155 059.

According to another particular embodiment, n-dodecane such as the product sold under the reference Parafol 12-97 by Sasol is used.

According to another particular embodiment, n-tetradecane such as the product sold under the reference Parafol 14-97 by Sasol is used.

According to yet another embodiment, a mixture of n-dodecane and n-tetradecane is used.

The esters are preferably branched esters chosen from esters of a branched alcohol and of a carboxylic acid.

In particular, mention may be made of:
  optionally hydroxylated diesters of a $C_2$-$C_8$ dicarboxylic acid and of a branched $C_2$-$C_8$ alcohol; such as diisopropyl adipate, bis(2-ethylhexyl)adipate, dibutyl adipate or diisostearyl adipate,
  esters of a monocarboxylic acid containing from 4 to 6 carbon atoms and of a branched alcohol containing from 12 to 26 carbon atoms, for instance isostearyl neopentanoate, tridecyl neopentanoate, isocetyl neopentanoate or isoarachidyl neopentanoate, and mixtures thereof.

According to one advantageous embodiment, the first hydrocarbon-based oil is chosen from isohexadecane, a mixture of at least two different linear alkanes, which are preferably volatile, containing from 10 to 14 carbon atoms and differing from each other by a carbon number of at least 1, in particular an n-undecane/n-tridecane mixture, diisopropyl adipate or isostearyl neopentanoate, and mixtures thereof.

Second Hydrocarbon-Based Oil

The second hydrocarbon-based oil is chosen from branched esters, pentaerythritol esters, hydrogenated polyolefins and fatty acid triglycerides, and mixtures thereof. According to one particular embodiment of the invention, the second hydrocarbon-based oil is chosen from pentaerythritol esters, hydrogenated polyolefins and fatty acid triglycerides, and mixtures thereof, Branched esters that may be used in particular include isostearyl neopentanoate and pentaerythrityl tetraoctanoate, for instance Dub VCI 18 from the company Stéarineries Dubois.

The pentaerythritol esters used in the composition according to the invention are preferably chosen from tetraesters derived from the reaction of pentaerythritol with linear or branched, saturated or unsaturated acids containing from 3 to 24 carbon atoms, preferably from 4 to 18 carbon atoms and even more preferentially from 5 to 10 carbon atoms, for instance 2-ethylhexanoic acid (octanoic acid).

A pentaerythritol ester that may be used in particular is pentaerythrityl tetraoctanoate, for instance Dub PTO from the company Stéarineries Dubois.

The hydrogenated polyolefins are in particular poly-α-olefins and more particularly of polybutene type chosen from hydrogenated polyisobutenes preferably comprising from 4 to 20 and preferably from 4 to 10 isobutene units.

An example that may be mentioned is Parleam® oil sold by the company NOF Corporation.

The fatty acid triglycerides may be chosen from liquid triglycerides of fatty acids containing from 4 to 10 carbon atoms, for instance heptanoic or octanoic acid triglycerides, or alternatively, for example, sunflower oil, maize oil, soybean oil, marrow oil, grapeseed oil, sesame seed oil, hazelnut oil, apricot oil, macadamia oil, arara oil, coriander oil, castor oil, avocado oil, caprylic/capric acid triglycerides, for instance those sold by the company Stearineries Dubois or those sold under the names Miglyol 810, 812 and 818 by the company Dynamit Nobel, jojoba oil, shea butter oil and the liquid fractions of shea butter. The liquid fraction of shea butter is used in particular, for instance Lipex 202 sold by the company Aarhuskarlshamn.

According to one advantageous embodiment, the second hydrocarbon-based oil is chosen from pentaerythrityl tetraoctanoate, hydrogenated polyisobutenes preferably comprising from 4 to 20 and preferably from 4 to 10 isobutene units, and the liquid fractions of shea butter, and mixtures thereof.

According to one particular embodiment, the composition according to the invention comprises at least a first hydrocarbon-based oil chosen from pentaerythritol esters, hydrogenated polyolefins and fatty acid triglycerides, and mixtures thereof, and at least a second hydrocarbon-based oil chosen from branched esters, pentaerythritol esters, hydrogenated polyolefins and fatty acid triglycerides, and mixtures thereof.

According to one advantageous embodiment, the composition according to the invention comprises:
- at least a first hydrocarbon-based oil chosen from isohexadecane, a mixture of at least two different linear alkanes, which are preferably volatile, containing from 10 to 14 carbon atoms and differing from each other by a carbon number of at least 1, in particular an n-undecane/n-tridecane mixture, diisopropyl adipate or isostearyl neopentanoate, and mixtures thereof,
- in a content of greater than or equal to 40% by weight of the mixture of first and second hydrocarbon-based oils, and
- at least a second hydrocarbon-based oil chosen from pentaerythrityl tetraoctanoate, hydrogenated polyisobutenes preferably comprising from 4 to 20 and preferably from 4 to 10 isobutene units, and the liquid fractions of shea butter, and mixtures thereof.

According to one embodiment, the composition comprises:
- at least a first hydrocarbon-based oil chosen from isohexadecane, a mixture of at least two different linear alkanes, which are preferably volatile, containing from 10 to 14 carbon atoms and differing from each other by a carbon number of at least 1, in particular an n-undecane/n-tridecane mixture, diisopropyl adipate or isostearyl neopentanoate, and mixtures thereof,
- in a content ranging from 40% to 80%, preferably from 50% to 70% by weight and better still from 55% to 65% by weight relative to the weight of the mixture of first and second hydrocarbon-based oils, and
- at least a second hydrocarbon-based oil chosen from pentaerythritol esters, preferably pentaerythrityl tetraoctanoate, in a content ranging from 20% to 59%, preferably from 30% to 50% by weight and better still from 35% to 45% by weight relative to the weight of the mixture of first and second hydrocarbon-based oils.

In particular, the composition comprises:
- at least a first hydrocarbon-based oil preferably chosen from isohexadecane, a mixture of at least two different linear alkanes, which are preferably volatile, containing from 10 to 14 carbon atoms and differing from each other by a carbon number of at least 1, in particular an n-undecane/n-tridecane mixture, diisopropyl adipate or isostearyl neopentanoate, and mixtures thereof,
- in a content ranging from 55% to 65% by weight of the mixture of first and second hydrocarbon-based oils, and
- at least a second hydrocarbon-based oil chosen from pentaerythrityl tetraoctanoate, in a content ranging from 35% to 45% by weight relative to the weight of the mixture of first and second hydrocarbon-based oils.

According to another embodiment, the composition comprises:
- at least a first hydrocarbon-based oil chosen from isohexadecane, a mixture of at least two different linear alkanes, which are preferably volatile, containing from 10 to 14 carbon atoms and differing from each other by a carbon number of at least 1, in particular an n-undecane/n-tridecane mixture, diisopropyl adipate or isostearyl neopentanoate, and mixtures thereof,
- in a content ranging from 40% to 80%, preferably from 50% to 70% by weight and better still from 55% to 65% by weight relative to the weight of the mixture of first and second hydrocarbon-based oils, and
- at least a second hydrocarbon-based oil chosen from hydrogenated polyolefins, more particularly chosen from hydrogenated polyisobutenes, preferably comprising from 4 to 20 and preferably from 4 to 10 isobutene units, in a content ranging from 20% to 59%, preferably from 30% to 50% by weight and better still from 35% to 45% by weight relative to the weight of the mixture of first and second hydrocarbon-based oils.

In particular, the composition comprises:
- at least a first hydrocarbon-based oil chosen from isohexadecane, a mixture of at least two different linear alkanes, which are preferably volatile, containing from 10 to 14 carbon atoms and differing from each other by a carbon number of at least 1, in particular an n-undecane/n-tridecane mixture, diisopropyl adipate or isostearyl neopentanoate, and mixtures thereof,
- in a content ranging from 55% to 65% by weight of the mixture of first and second hydrocarbon-based oils, and
- at least a second hydrocarbon-based oil chosen from hydrogenated polyisobutenes, preferably comprising from 4 to 20 and preferably from 4 to 10 isobutene units, in a content ranging from 35% to 45% by weight relative to the weight of the mixture of first and second hydrocarbon-based oils.

According to another embodiment, the composition comprises:
- at least a first hydrocarbon-based oil chosen from isohexadecane, a mixture of at least two different linear alkanes, which are preferably volatile, containing from 10 to 14 carbon atoms and differing from each other by a carbon number of at least 1, in particular an n-undecane/n-tridecane mixture, diisopropyl adipate or isostearyl neopentanoate, and mixtures thereof,
- in a content ranging from 40% to 80%, preferably from 50% to 70% by weight and better still from 55% to 65% by weight relative to the weight of the mixture of first and second hydrocarbon-based oils, and
- at least a second hydrocarbon-based oil chosen from liquid triglycerides of fatty acids comprising from 4 to 10 carbon atoms, for instance heptanoic or octanoic acid triglycerides or, for example, sunflower oil, corn oil, soybean oil, marrow oil, grapeseed oil, sesame seed oil, hazelnut oil, apricot oil, macadamia oil, arara oil, coriander oil, castor oil, avocado oil, caprylic/capric acid triglycerides, jojoba oil, shea butter oil and the liquid fractions of shea butter, in a content ranging from 20% to 59%, preferably from 30% to 50% by weight and better still from 35% to 45% by weight relative to the weight of the mixture of first and second hydrocarbon-based oils.

In particular, the composition comprises:
- at least a first hydrocarbon-based oil chosen from isohexadecane, a mixture of at least two different linear alkanes, which are preferably volatile, containing from 10 to 14 carbon atoms and differing from each other by a carbon number of at least 1, in particular an n-undecane/n-tridecane mixture, diisopropyl adipate or isostearyl neopentanoate, and mixtures thereof,
in a content ranging from 55% to 65% by weight of the mixture of first and second hydrocarbon-based oils, and
at least a second hydrocarbon-based oil chosen from the liquid fractions of shea butter, in a content ranging from 35% to 45% by weight relative to the weight of the mixture of first and second hydrocarbon-based oils.

The composition according to the invention may comprise the mixture (first and second hydrocarbon-based oils and silica aerogel particles) in a content ranging from 0.1% to 90% by weight, preferably from 1% to 80% by weight, better still from 2% to 30% by weight and even better still from 2% to 20% by weight, relative to the total weight of the composition.

The composition according to the invention may be aqueous or anhydrous.

The composition according to the invention may be in any galenical form conventionally used for topical application and especially in the form of dispersions of the aqueous lotion or gel type, emulsions of liquid or semi-liquid consistency of the milk type, obtained by dispersing a fatty phase in an aqueous phase (O/W) or conversely (W/O), or suspensions or emulsions of soft, semi-solid or solid consistency of the cream or gel type, or alternatively multiple emulsions (W/O/W or O/W/O), microemulsions, vesicular dispersions of ionic and/or nonionic type, or wax/aqueous phase dispersions. It may also be in the form of hot-cast sticks, and loose or compacted powders.

These compositions are prepared according to the usual methods.

According to one embodiment of the invention, the composition is in the form of an O/W emulsion or an aqueous gel.

The compositions of the invention may be used in any cosmetic or dermatological application, for example in cosmetics for caring for the skin, the hair, the scalp, the eyelashes, the eyebrows, the nails or mucous membranes (the lips), for example as protecting, treating or care products for the face, the hands or the body, as skin-cleansing products (for the face or the body), as makeup products (for example foundations) or as haircare products.

The composition according to the invention may comprise, besides the first and second hydrocarbon-based oils of the mixture (silica aerogel particles and hydrocarbon-based oils), at least one "additional" oil. The term "oil" means a fatty substance that is liquid at room temperature (25° C.).

As oils that may be used in the composition of the invention, examples that may be mentioned include:
hydrocarbon-based oils of animal origin, such as perhydrosqualene (or squalane);
synthetic esters and ethers, especially of fatty acids or of fatty alcohols, for instance the oils of formulae $R^1COOR^1$ and $R^1OR^1$ in which $R^1$ represents a fatty acid residue containing from 8 to 29 carbon atoms and $R^2$ represents a branched or unbranched hydrocarbon-based chain containing from 3 to 30 carbon atoms, for instance purcellin oil, isononyl isononanoate, isopropyl myristate, 2-ethylhexyl palmitate (or octyl palmitate), 2-octyldodecyl stearate, 2-octyldodecyl erucate or isostearyl isostearate; hydroxylated esters, for instance isostearyl lactate, octyl hydroxystearate, octyldodecyl hydroxystearate, diisostearyl malate, triisocetyl citrate, and fatty alkyl heptanoates, octanoates and decanoates; polyol esters, for instance propylene glycol dioctanoate, neopentyl glycol diheptanoate and diethylene glycol diisononanoate; lipophilic amino acid derivatives, such as isopropyl lauroyl sarcosinate (INCI name: Isopropyl Lauroyl Sarcosinate) sold under the name Eldew SL 205 by the company Ajinomoto;
fatty alcohols containing from 8 to 26 carbon atoms, for instance cetyl alcohol, stearyl alcohol and a mixture thereof (cetylstearyl alcohol), octyldodecanol, 2-butyloctanol, 2-hexyldecanol, 2-undecylpentadecanol or oleyl alcohol;
partially hydrocarbon-based and/or silicone-based fluoro oils, for instance those described in document JP-A-2 295 912;
silicone oils, for instance volatile or non-volatile, linear or cyclic polydimethylsiloxanes (PDMS); polydimethylsiloxanes comprising alkyl, alkoxy or phenyl groups, which are pendent or at the end of a silicone chain, these groups containing from 2 to 24 carbon atoms; phenyl silicones, for instance phenyl trimethicones, phenyl dimethicones, phenyltrimethylsiloxydiphenylsiloxanes, diphenyl dimethicones, diphenylmethyldiphenyltrisiloxanes and 2-phenylethyltrimethyl siloxysilicates;
mixtures thereof.

The other fatty substances that may be present in the oily phase are, for example, fatty acids comprising from 8 to 30 carbon atoms, for instance stearic acid, lauric acid or palmitic acid; gums such as silicone gums (dimethiconol); silicone resins such as trifluoromethyl-C1-4-alkyldimethicone and trifluoropropyl dimethicone; pastes such as petrolatum; waxes such as microcrystalline waxes, paraffin waxes, lignite waxes, ceresin, ozokerites, montan wax, beeswax, lanolin and derivatives thereof, candelilla wax, ouricurry wax, carnauba wax, Japan wax, cocoa butter, palm oil in paste form at 20° C., cork fibre wax, sugar cane wax, hydrogenated oils that are solid at 25° C., fatty esters and triglycerides that are solid at 25° C., polyethylene waxes, the waxes obtained by Fischer-Tropsch synthesis, and silicone waxes; and mixtures of these fatty substances.

According to one embodiment, the composition according to the invention comprises less than 2% by weight and preferably less than 1% by weight of silicone elastomer solids, and better still is free of silicone elastomers.

Silicone Elastomers or Elastomeric Organopolysiloxanes

The term "elastomer" means a deformable, flexible organopolysiloxane with viscoelastic properties and especially the consistency of a sponge or of a supple sphere. Its modulus of elasticity is such that this material withstands deformation and has limited stretchability and contractability. This material is capable of regaining its original shape after stretching. This elastomer is formed from chains of high molecular weight polymer, the mobility of which is limited by a uniform network of crosslinking points.

Elastomeric organopolysiloxanes are generally partially or totally crosslinked and may be in the form of particles.

Such elastomers are, for example, the products sold under the name KSG by the company Shin-Etsu, under the name Trefil by the company Dow Corning or under the name Gransil by the company Grant Industries.

The composition according to the invention may comprise an aqueous phase, the amount of which may range, for example, from 30% to 98% by weight, preferably from 40% to 98% by weight, better still from 50% to 98% by weight and even better still from 55% to 98% by weight relative to the total weight of the composition.

Conventionally, the aqueous phase may contain, besides water, one or more water-soluble solvents chosen from polyols (or polyhydric alcohols) and water-soluble lower alcohols, and mixtures thereof. The term "lower alcohol" means an alcohol comprising from 1 to 8 and preferably from 1 to 6 carbon atoms. Examples of lower alcohols that may be mentioned include isopropanol and butanol, and mixtures thereof.

Examples of polyols that may be mentioned include glycerol; glycols such as propylene glycol or butylene glycol; sorbitol; sugars such as glucose, fructose, maltose, lactose and sucrose; and mixtures thereof.

The amount of water-soluble solvents (lower alcohols and polyols) may range, for example, from 0.5% to 30% by weight, preferably from 0.5% to 20% by weight and better still from 1% to 15% by weight relative to the total weight of the composition.

Adjuvants

In a known manner, the composition of the invention may also contain adjuvants that are common in cosmetics and/or dermatology, such as active agents, preserving agents, antioxidants, complexing agents, pH modifiers (acidic or basic), fragrances, mineral or organic fillers (other than the silica aerogels), bactericides, odour absorbers, dyestuffs (pigments and dyes), film-forming polymers, emulsifiers such as fatty acid esters of polyethylene glycol, fatty acid esters of glycerol and fatty acid esters of sorbitan, which are optionally polyoxyethylenated, polyoxyethylenated fatty alcohols and esters or ethers of fatty acids and of sugars such as sucrose or glucose; thickeners and/or gelling agents, in particular polyacrylamides, acrylic homopolymers and copolymers, and acrylamidomethylpropanesulfonic acid homopolymers and copolymers, and also lipid vesicles. The amounts of these various adjuvants are those conventionally used in the field under consideration, for example from 0.01% to 20% of the total weight of the composition. Depending on their nature, these adjuvants may be introduced into the fatty phase, into the aqueous phase and/or into the lipid vesicles.

Among the mineral fillers, other than the hydrophobic silica aerogels, which may be used in the compositions according to the invention, mention may be made of talc, mica, silica, trimethyl siloxysilicate, kaolin, bentone, calcium carbonate, magnesium hydrogen carbonate, hydroxyapatite, boron nitride, hollow silica microspheres (Silica Beads from Maprecos), glass or ceramic microcapsules, silica-based fillers, for instance Aerosil 200 or Aerosil 300; Sunsphere H-33 and Sunsphere H-51 sold by Asahi Glass; Chemicelen sold by Asahi Chemical; composites of silica and of titanium dioxide, for instance the TSG series sold by Nippon Sheet Glass, and mixtures thereof.

Among the organic fillers that may be used in the compositions according to the invention, mention may be made of polyamide powder (Nylon® Orgasol from Atochem), poly-β-alanine powder and polyethylene powder, polytetrafluoroethylene (Teflon®) powder, lauroyllysine, starch, tetrafluoroethylene polymer powders, hollow polymer microspheres, such as Expancel (from Nobel Industrie), metal soaps derived from organic carboxylic acids containing from 8 to 22 carbon atoms and preferably from 12 to 18 carbon atoms, for example zinc stearate, magnesium stearate, lithium stearate, zinc laurate or magnesium myristate, Polypore® L200 (Chemdal Corporation), silicone resin microbeads (for example Tospearl® from Toshiba), polyurethane powders, in particular microwaxes formed from a mixture of carnauba wax and polyethylene wax, such as the products sold under the names MicroCare 300® and 310® by the company Micro Powders, microwaxes formed from a mixture of carnauba wax and synthetic wax, such as the product sold under the name MicroCare 325® by the company Micro Powders, polyethylene microwaxes, such as those sold under the names Micropoly 200®, 220®, 220L® and 250S® by the company Micro Powders; and mixtures thereof.

Needless to say, a person skilled in the art will take care to select this or these optional additional compound(s), and/or the amount thereof, such that the matting/soft focus properties of the composition according to the invention are not, or are not substantially, adversely affected by the envisaged addition.

In the patent application, unless specifically mentioned otherwise, the contents are expressed on a weight basis relative to the total weight of the composition.

The examples that follow are aimed at illustrating the compositions and processes according to this invention, but are not in any way a limitation of the scope of the invention. All the parts and percentages in the examples are given on a weight basis and all the measurements were obtained at about 25° C., unless otherwise mentioned.

EXAMPLE 1

25 compositions were prepared, each comprising 8% of hydrophobic silica aerogels particles (VM-2270 from Dow Corning) and 92% of a mixture of the following hydrocarbon-based oils.

| Mixture: | 2-Octyldodecanol | Isohexadecane (from Ineos) | Pentaerythrityl tetraoctanoate (Dub PTO from Stearineries Dubois) | Liquid fraction of shea butter (Lipex 202 from Aarhuskarlshamn) | Hydrogenated polyisobutene (Parleam from NOF) | Macroscopic appearance | Appearance after application to the skin |
|---|---|---|---|---|---|---|---|
| 1 | 60 | 40 | | | | σ | ν |
| 2 | 60 | | 40 | | | σ | ν |
| 3 | 60 | | | 40 | | σ | ν |
| 4 | 60 | | | | 40 | μ | ν |
| 5 | | 60 | 40 | | | σ | ι |
| 6 | | 60 | | 40 | | σ | ι |
| 7 | | 60 | | | 40 | σ | ι |
| 8 | 40 | 60 | | | | σ | ν |
| 9 | | | 60 | 40 | | σ | ν |
| 10 | | | 60 | | 40 | λ | x |
| 11 | 40 | | 60 | | | σ | ν |
| 12 | | 40 | 60 | | | σ | ν |
| 13 | | | | 60 | 40 | σ | ν |
| 14 | 40 | | | 60 | | σ | ν |
| 15 | | 40 | | 60 | | σ | ν |
| 16 | | | 40 | 60 | | σ | ν |
| 17 | 40 | | | | 60 | μ | ν |
| 18 | | 40 | | | 60 | σ | ν |

-continued

| Mixture: | 2-Octyldodecanol | Isohexadecane (from Ineos) | Pentaerythrityl tetraoctanoate (Dub PTO from Stearineries Dubois) | Liquid fraction of shea butter (Lipex 202 from Aarhuskarlshamn) | Hydrogenated polyisobutene (Parleam from NOF) | Macroscopic appearance | Appearance after application to the skin |
|---|---|---|---|---|---|---|---|
| 19 | | | 40 | | 60 | σ | ν |
| 20 | | | | 40 | 60 | σ | ν |
| 21 | 100 | | | | | μ | ν |
| 22 | | 100 | | | | σ | ν |
| 23 | | | 100 | | | σ | ν |
| 24 | | | | 100 | | σ | ν |
| 25 | | | | | 100 | σ | ν |

σ: gel that does not flow;
μ: gel that flows;
λ non-homogeneous sample;
ι: matt;
ν: shiny;
x: not applicable The compositions are obtained by introducing the silica aerogel particles with gentle paddle stirring.

These compositions were evaluated visually by three individuals who then applied each composition to the back of the hand and gave a matt/shiny note in comparison with bare skin.

Only the compositions comprising the mixtures 5, 6 and 7 according to the invention are in the form of a gel which does not flow and which, when applied to the skin, is characterized by a matt, soft-focus deposit.

EXAMPLE 2

Cream for Greasy Skin

| Phase | INCI name | |
|---|---|---|
| A | Water | qs 100 |
| | Glycerol | 5.00 |
| | Disodium EDTA | 0.05 |
| | Propylene glycol | 6.60 |
| B | Caprylyl glycol | 0.15 |
| | Isohexadecane | 9.06 |
| | Polysorbate 80 (Tween 80-LQ-(WL) from Croda) | 1.00 |
| | Dimethicone (and) ceteth-10 (and) laureth-4 (Dow Corning 7-3099 Dimethicone HIP Emulsion) | 1.50 |
| | Pentaerythrityl tetraoctanoate | 3.68 |
| C | Isohexadecane | 1.00 |
| | Carbomer (Carbopol 981 from Lubrizol) | 0.15 |
| D | Sodium hydroxide | 0.06 |
| | Water | 0.54 |
| | Ammonium polyacryloyldimethyltaurate (Hostacerin AMPS from Clariant) | 1.80 |
| E | Nylon-12 (Orgasol 2002 EXD NAT COS from Arkema) | 0.50 |
| | Ethanol | 5.00 |
| G | Hydrophobic silica aerogel particles (VM-2270 from Dow Corning) | 0.8 |

Procedure:
heat phase B to about 70° C.,
heat phase A to about 70° C.,
prepare the emulsion by incorporating phase A into phase B,
at 40-45° C. incorporate the remaining phases and continue stirring until cooling is complete.

EXAMPLE 3

Moisturizing Cream

| Phase | INCI name | |
|---|---|---|
| A1 | Water | qs 100 |
| | Butylene glycol | 5.00 |
| | Glycerol | 5.00 |
| | Tetrasodium EDTA | 0.20 |
| | Phenoxyethanol | 0.70 |
| B | Glyceryl stearate (and) PEG-100 stearate (Arlacel 165-FL from Croda) | 2.00 |
| | Cetyl alcohol | 0.50 |
| | Methyl paraben | 0.25 |
| | PEG-20 stearate (Myrj S20-PA-(WL) from Croda) | 0.80 |
| | Stearyl alcohol | 0.50 |
| | Stearic acid | 3.00 |
| | Capryloyl salicylic acid (Mexoryl SAB from Chimex) | 0.05 |
| | Ammonium polyacryloyldimethyltaurate (Hostacerin AMPS from Clariant) | 1.60 |
| | Isohexadecane | 4.41 |
| | Parleam | 2.94 |
| B2 | Triethanolamine | 0.30 |
| B3 | Hydrophobic silica aerogel particles (VM-2270 from Dow Corning) | 0.64 |

Procedure:
heat phase B to about 75° C.,
heat phase A to about 75° C.,
prepare the emulsion by incorporating phase A into phase B,
at 40-45° C. incorporate the remaining phases and continue stirring until cooling is complete.

The creams of Examples 2 and 3 are comfortable and gentle on application, and give a good matting effect on the skin.

EXAMPLE 4

Cream for Greasy Skin

| Phase | INCI name | Formula per 100 g |
|---|---|---|
| A | WATER | 68.85 |
|  | GLYCEROL | 7.00 |
|  | Propylene glycol | 2.00 |
| B | Ammonium polyacryloyldimethyl taurate | 1.00 |
| C | Pentaerythrityl tetrakis(ethylhexanoate) | 3.60 |
|  | Isostearyl neopentanoate | 5.60 |
|  | PEG-12 Dimethicone | 0.70 |
| D | Biosaccharide Gum-1 | 2.00 |
| E | Caprylyl glycol | 0.40 |
|  | Menthol | 0.05 |
|  | Denatured alcohol | 8.00 |
| F | Silica Silylate | 0.80 |

Procedure:
heat phase B to about 70° C.,
heat phase A to about 70° C.,
prepare the emulsion by incorporating phase A into phase B,
at 40-45° C., incorporate the remaining phases and continue stirring until cooling is complete.

COMPARATIVE EXAMPLE 5

| INCI NAME | Composition a | Composition b | Composition c | Composition d | Composition e |
|---|---|---|---|---|---|
| MENTHOL | 0.05 | 0.05 | 0.05 | 0.05 | 0.05 |
| SILICA SILYLATE (DOW CORNING VM-2270) | 0.8 | 0.8 | 0.8 | 0.8 | 0.8 |
| PENTAERYTHRITYL TETRAETHYLHEXANOATE | — | — | — | 9.2 | 3.6 |
| ISOHEXADECANE | — | 9.2 | 5.6 | — | 5.6 |
| HYDROGENATED POLYISOBUTENE (Parleam de NOF CORPORATION) | 9.2 | — | 3.6 | — | — |
| AMMONIUM POLYACRYLOYLDIMETHYL TAURATE (HOSTACERIN AMPS de Clariant) | 1 | 1 | 1 | 1 | 1 |
| BIOSACCHARIDE GUM-1 (Fucogel 1.5P de SOLABIA) | 2 | 2 | 2 | 2 | 2 |
| PEG-12 DIMETHICONE (Silsoft 880 de MOMENTIVE PERFORMANCE MATERIALS) | 0.7 | 0.7 | 0.7 | 0.7 | 0.7 |
| ALCOHOL DENAT. | 8 | 8 | 8 | 8 | 8 |
| WATER | 68.85 | 68.85 | 68.85 | 68.85 | 68.85 |
| GLYCERIN | 7 | 7 | 7 | 7 | 7 |
| PROPYLENE GLYCOL | 2 | 2 | 2 | 2 | 2 |
| CAPRYLYL GLYCOL | 0.4 | 0.4 | 0.4 | 0.4 | 0.4 |

The sample is applied in a thick layer of 30 or 60 μm on a contrast card (24/5-250 cm ERICHSEN of PRUFKARTE type). The films were then dried for 10 minutes at 37° C., measurements are then performed in triplicate on the white card contrast. The Glossmeter (micro-TRI-brillant of BYK Gardner) is a device that allows a rapid measurement of the brightness of the sample. The device illuminates the sample and measures the intensity of specular reflection. This measure is then normalized to a standard and converted to a given value of brightness in arbitrary units (UB) The lower the value, the lower the sample is brilliant.

Results of Brightness Measurements:

|  | Brightness (ub), layer of 60 μm |
|---|---|
| Composition a | 10.5 |
| Composition b | 10 |
| Composition c (invention) | 6.5 |

|  | Brightness (ub), layer of 30 μm |
|---|---|
| Composition d | 16 |
| Composition b | 18 |
| Composition e (invention) | 12 |

These results show that the desired effect of correcting skin imperfections (matt, soft-focus) is not obtained when the hydrophobic silica aerogel is associated with only one oil.

The invention claimed is:
1. A cosmetic composition, comprising:
trimethylsilyl silica particles with a specific surface area per unit of mass (SM) ranging from 600 to 800 $m^2/g$ and a size expressed as the mean volume diameter (D[0.5]) ranging from 5 to 20 μm,
at least a first hydrocarbon-based oil selected from the group consisting of isohexadecane, isododecane, and a mixture of at least two different linear alkanes containing from 10 to 14 carbon atoms and differing from each other by a carbon number of at least 1, and
at least a second hydrocarbon-based oil selected from the group consisting of pentaerythrityl tetraoctanoate, isostearyl neopentanoate, a hydrogenated polyisobutene, a liquid fraction of shea butter, and apricot oil,
wherein the first hydrocarbon-based oil is present in a content of greater than or equal to 40% by weight of the total weight of the first and second hydrocarbon-based oils, and wherein the trimethylsilyl silica particles present in an amount of 0.5% to 10% by weight of the total weight of the trimethylsilyl silica particles, the first hydrocarbon-based oil and the second hydrocarbon-based oil.

2. The composition of claim 1, wherein the hydrophobic silica aerogel particles have a tamped density ranging from 0.04 g/cm$^3$ to 0.10 g/cm$^3$.

3. The composition of claim 1, wherein the hydrophobic silica aerogel particles have an oil-absorbing capacity, measured at the wet point, ranging from 5 to 18 ml/g.

4. The composition of claim 1, wherein the first and second hydrocarbon-based oils represent from 80% to 99% by weight relative to the total weight of the trimethylsilyl silica particles, the first hydrocarbon-based oil and the second hydrocarbon-based oil.

5. The composition of claim 1, wherein the first hydrocarbon-based oil is present in a content of greater than or equal to 50% by weight of the total weight of the first hydrocarbon-based oil and the second hydrocarbon-based oil.

6. The composition of claim 1, wherein the first hydrocarbon-based oil is present in a content ranging from 40% to 80% by weight of the total weight of the first hydrocarbon-based oil and the second hydrocarbon-based oil.

7. The composition of claim 1, wherein the second hydrocarbon-based oil is present in a content ranging from 20% to 59% by weight of the total weight of the first hydrocarbon-based oil and the second hydrocarbon-based oil.

8. A cosmetic process for making up and/or caring for keratin materials, the process comprising applying the composition of claim 1 to the said materials.

9. The composition of claim 1, which is the form of a gel.

10. The composition of claim 1, wherein the second hydrocarbon-based oil comprises a liquid fraction of shea butter.

* * * * *